United States Patent [19]

Karasawa

[11] 4,357,079
[45] Nov. 2, 1982

[54] SLIT PATTERN PROJECTING APPARATUS HAVING ALIGNMENT DETECTING MEANS

[75] Inventor: Yukinori Karasawa, Tokyo, Japan

[73] Assignee: Tokyo Kogaku Kikai Kabushiki Kaisha, Tokyo, Japan

[21] Appl. No.: 87,238

[22] Filed: Oct. 22, 1979

[30] Foreign Application Priority Data

Oct. 24, 1978 [JP] Japan ................................ 53-130736

[51] Int. Cl.³ .......................... A61B 3/14; A61B 3/10; G03B 29/00
[52] U.S. Cl. ......................................... 351/7; 351/14; 351/16; 354/62
[58] Field of Search ........................... 351/14, 16, 6, 7; 354/62

[56] References Cited

U.S. PATENT DOCUMENTS

| | | | |
|---|---|---|---|
| 4,175,839 | 11/1979 | Müller et al. | 351/14 |
| 4,219,258 | 8/1980 | Araki et al. | 351/7 X |
| 4,252,420 | 2/1981 | Kohayakawa | 351/7 |
| 4,257,687 | 3/1981 | Kohayakawa | 351/7 |

Primary Examiner—John K. Corbin
Assistant Examiner—Rodney Bovernick
Attorney, Agent, or Firm—Stevens, Davis, Miller & Mosher

[57] ABSTRACT

A slit lamp device having a slit pattern projecting optical system for projecting an illumination light in a pattern of a slit to a patient's eye. An alignment detecting device is provided for detecting the alignment between the optical axis of the projecting system and the axis of the patient's eye. The device comprises one or more light receiving elements such as phototransistors which are located at one or both sides of the projecting optical axis and in the slit plane.

8 Claims, 8 Drawing Figures

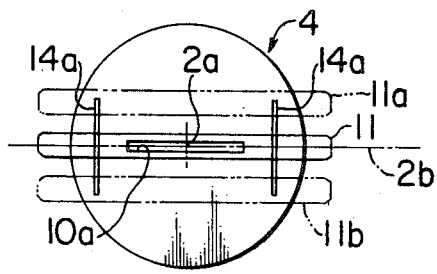
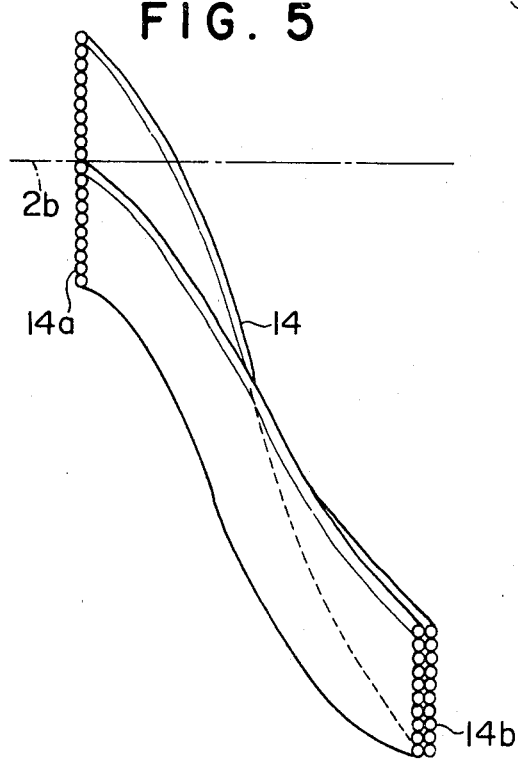
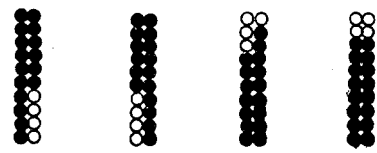
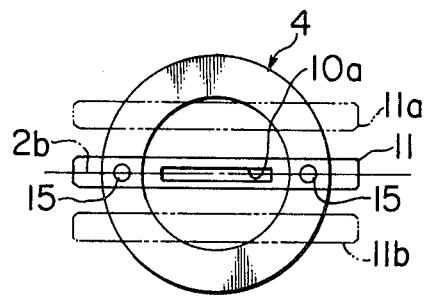
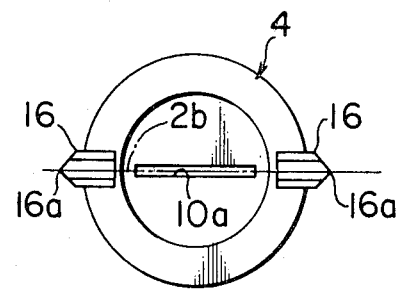

SLIT PATTERN PROJECTING APPARATUS HAVING ALIGNMENT DETECTING MEANS

The present invention relates to slit pattern projecting devices and more particularly to alignment detecting means for slit pattern projecting devices.

For example, an apparatus for taking photographs of sections of crystalline lenses of patient's eyes includes a slit pattern projecting optical system for projecting an illumination light in a pattern of a slit to the patient's eye and a photographing optical system having an optical axis obliquely directed to the plane of the slit pattern for taking photographs of the illuminated section of the crystalline lens. In this type of apparatus, it is possible to take photographs of crystalline lens sections in any angular orientation by rotating the apparatus with respect to the patient's eye about the optical axis of the slit pattern projecting system. If, however, there is any misalignment between the optical axis of the slit pattern projecting system and the optical axis of the patient's eye, there will be produced a shadow area which cannot be photographed. It is therefore very important to establish an accurate alignment between the optical axis of the slit projecting system and the optical axis of the patient's eye. Even if the apparatus is of such a type that is not designed for rotation about the slit projecting optical axis, the aforementioned alignment is important for an accurate observation.

It is therefore an object of the present invention to provide simple and reliable means in a slit pattern projecting device for detecting the alignment between the slit projecting optical axis and the axis of the patient's eye.

According to the present invention, the above and other objects can be accomplished by a slit pattern projecting apparatus including objective means having an optical axis and adapted to be placed adjacent a patient's eye, means for projecting a slit pattern light through said objective means to said patient's eye along a slit plane which contains said optical axis of the objective means, alignment detecting means comprising light receiving means including at least one light receiving element located at least in said slit plane at least at one side of the optical axis. In a preferable mode of the present invention the light receiving means may be comprised of a plurality of light receiving elements such as photo-transistors or ends of optical fibers which are arranged in one or more rows extending perpendicularly to the slit plane. Such light receiving elements may be located preferably at the opposite sides of the optical axis. Alternatively, the light receiving means may comprise one or more plates such as frosted glasses which facilitate indentification of the location of light as reflected at the corneal surface of the patient's eye.

In case where the apparatus is not rotatable about the optical axis of the objective means, the light receiving elements may be located only at one side of the optical axis. However, where the apparatus is rotatable about the optical axis, it is preferable to locate the light receiving elements at the opposite sides of the optical axis because the elements at one side may be covered by a part of the apparatus when the apparatus is in a certain orientation.

For the purpose of the present invention, only one light receiving element may be provided in the slit plane at one side of the optical axis. However, to facilitate ready detection and adjustment of the alignment, it is preferable to provide a plurality of small light receiving elements which are arranged in one or more rows perpendicular to the slit plane so that the direction and degree of misalignment can be detected by knowing the element or elements which are actually receiving the light as reflected at the corneal surface of the patient's eye.

The alignment detecting means in accordance with the present invention is based on the fact that the light reflected at the corneal surface of the patient's eye proceeds along the slit plane but in the direction opposite to the projected light when the optical axis of the objective means is in alignment with the axis of the patient's eye, however, when the axis of the patient's eye is sidewardly offset from the slit plane, the reflected light is displaced from the slit plane in the direction of the sideward offset. Therefore, by arranging the light receiving elements in the aforementioned rows, it is possible to detect even the direction of the offset. Thus, adjustment alignment can be made very easily in accordance with the present invention.

In case where the light receiving means includes optical fibers, such fibers may preferably be used in the form of a sheet wherein the fibers are arranged in a row. One end of the sheet is then located in the slit plane to constitute the row of light receiving elements. The other end of the sheet may preferably be located in the eyepiece of the apparatus so that the position of the reflected light can readily be observed. In this instance, the other end of the sheet may be folded at the center thereof so that the exact alignment can readily be judged.

In case where the light receiving elements are constituted by photo-transistors, exact alignment can be indicated by means of a buzzer or an indication light. Where a plurality of phototransistors are arranged in a row, indication elements such as light emitting diodes may by provided for respective ones of the photo-transistors. The indication elements may be arranged in two rows as if a row of such elements is folded at the center thereof as in the case of the sheet of optical fibers.

The above and other objects and features of the present invention will become apparent from the following descriptions of preferred embodiments taking reference to the accompanying drawings, in which;

FIG. 4 is a front view of the objective lens assembly;

FIG. 5 is a diagrammatical view showing an arrangement of the optical fibers;

FIG. 6 is shows ends of the optical fibers in the eyepiece of the apparatus; and FIGS. 7 and 8 are front views of the objective lens assemblies in accordance with other embodiments.

Figure 1:
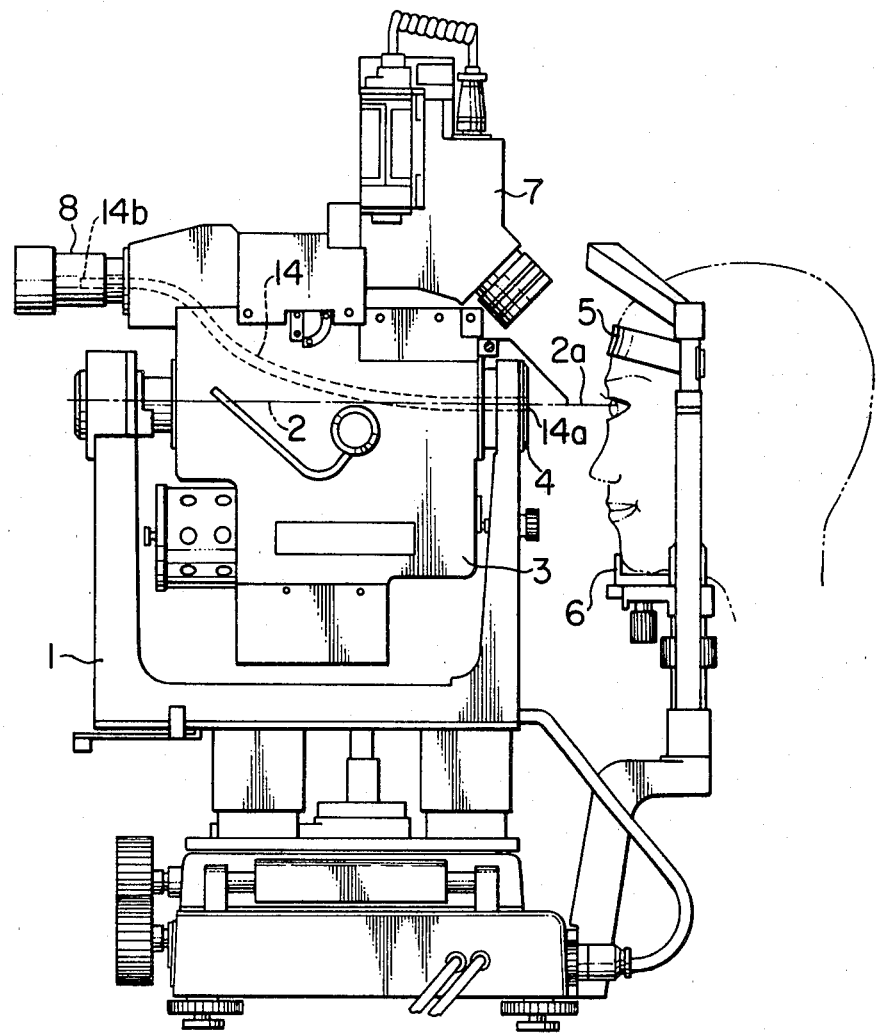
FIG. 1 is a side view of an apparatus for taking photographs of sections of crystalline lenses embodying the features of the present invention.
Figure 2:
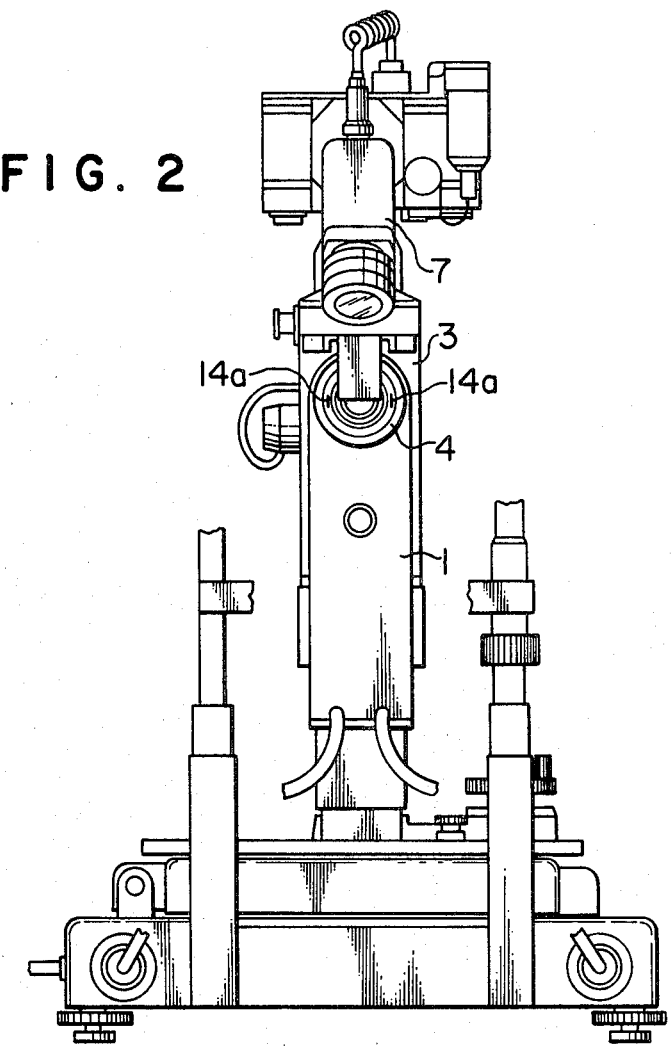
FIG. 2 is a front view of the apparatus shown in FIG. 1.

Referring to the drawings, particularly to FIGS. 1 and 2, there is shown an apparatus for taking photographs of patient's crystalline lenses in accordance with one embodiment of the present invention. The apparatus includes a support fixture 1 carrying a projector housing 3 for rotation about a horizontal axis 2. In the housing 3, there is provided an objective lens assembly 4 having a projecting optical axis 2a which is aligned with the horizontal axis 2. There is also provided in the housing 3 a slit pattern projecting optical system which may be of a conventional type. As an example, use may be made of a slit pattern projecting optical system as disclosed in U.S. Pat. No. 4,171,877 issued Oct. 23, 1979 and assigned to the same assignee of the present invention. Opposite to the objective lens assembly 4, there are provided a forehead rest 5 and a chin rest 6. A camera 7 is mounted on the projector housing 3 so that a photograph is taken in an oblique direction with respect to the projecting optical axis 2a. As shown in FIG. 1, the camera 7 has an eyepiece 8.

Figure 3:
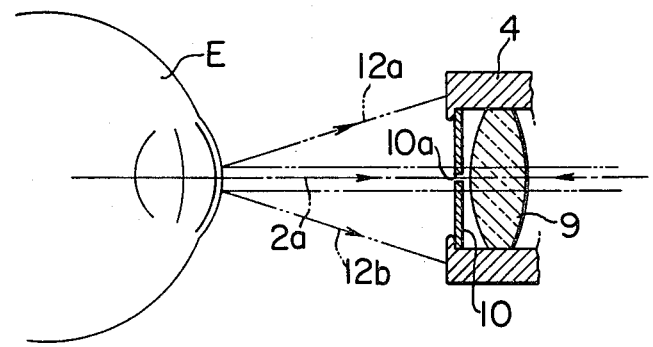
FIG. 3 is a sectional view showing the relationship between the objective lens assembly and the patient's eye.

Referring now to FIG. 3, it will be noted that the objective lens assembly 4 includes an objective lens 9 and a secondary slit plate 10 having a secondary slit aperture 10a so that the light is projected in the pattern of a flat sheet. The projected light is in part reflected at the corneal surface of the patient's eye E and the remainder of the light passes through the eye. Where the projecting axis 2a is in alignment with the axis of the eye E, the light reflected at the corneal surface proceeds in the direction opposite to the projected light along a plane 2b including the projecting axis 2a and the axis of the slit aperture 10a. The projected light may to a certain degree diverge before it impinges upon the objective lens assembly 4, however, due to the existence of the slit plate 10 in front of the objective lens 9, the amount of divergence is not so significant. Therefore, the reflected light impinges upon the front surface of the objective lens assembly 4 in a pattern as shown by 11 in FIG. 4. When the projecting optical axis 2a is offset upwards or downwards with respect to the axis of the patient's eye E, the reflected light proceeds as shown by 12a or 12b in FIG. 3 to produce an offset or displaced slit image as shown by 11a or 11b in FIG. 4.

In the illustrated embodiment, in order to detect the position of the reflected light, there is provided optical fiber sheets 14 each including a plurality of optical fibers arranged in a layer. The optical fiber sheets 14 have one group of ends 14a arranged at the opposite sides of the projecting optical axis substantially perpendicularly to the slit plane 2b. The other ends 14b of the optical fiber sheets 14 are located in the eyepiece 8 of the camera 7. It is preferable as shown in FIG. 5 to fold the sheet 14 at the end 14b along the center which corresponds to the slit plane 2b so that the same number of fibers are illuminated in the folded two rows when the projecting optical axis 2a is aligned with the optical axis of the patient's eye, as shown in FIG. 6(a). If there is any misalignment, different number of fibers are illuminated as shown in FIGS. 6(b), (c) and (d).

The ends of the fibers at the end 14a of the fiber sheet 14 may be substituted by phototransistors, and light emitting diodes may be provided for respective ones of the phototransistors. In such a case, the light emitting diodes may be arranged as in the case of the optical fiber ends in the end 14b of the sheet 14.

Referring now to FIG. 7 which shows another embodiment of the present invention, the objective lens assembly 4 is provided at the front surface with a pair of phototransistors 15 which are located in the slit plane 2b at the opposite sides of the projecting optical axis. The arrangement may be such that, when the reflected light impinges upon the phototransistor 15, an indication is made for example by a buzzer or indication light (not shown) to shown that an accurate alignment is established. For the purpose, a suitable electrical circuit may be provided.

FIG. 8 shows a further embodiment of the present invention. In this embodiment, a pair of light receiving plates 16 are provided in the place of the phototransistors 15 in the previous embodiment. Such plates 16 may be formed of frosted glasses, synthetic resin or any kind of material. The light pattern on the light receiving element is visually observed by the operator and, for the purpose of providing a ready observation, the plate 16 may be formed with a pointed end 16a or any other suitable mark for designating the slit plane 2b.

From the above descriptions, it will be noted that the alignment in vertical direction can be established with the slit plane 2b laid horizontally. For adjustment of the alignment in horizontal direction, the projector housing is rotated by 90° about the projecting optical axis.

The invention has thus been shown and described with reference to specific embodiments, however, it should be noted that the invention is in no way limited to the details of the illustrated arrangements but changes and modifications may be made without departing from the scope of the appended claims.

I claim:

1. Slit pattern projecting apparatus comprising objective lens means having an optical axis and means to position a patient's eye in fixed relation to said objective lens means, means for projecting a slit pattern light through said objective lens means to said patient's eye along a slit plane which contains said optical axis of the objective lens means, observing optical means having an observing optical axis obliquely intersecting said slit plane for observing a portion of said patient's eye which is being illuminated by said slit pattern light, alignment detecting means comprising light receiving means including at least one light receiving element located outside of said objective lens means and at least in said slit plane at least at one side of the objective lens means so that it receives the slit pattern of light as reflected at the patient's eye.

2. Slit pattern projecting apparatus in accordane with claim 1 in which said light receiving means includes a plurality of light receiving elements arranged in at least one row perpendicular to the slit plane.

3. Slit pattern projecting apparatus in accordance with claim 1 in which said light receiving element is a phototransistor.

4. Slit pattern projecting apparatus in accordance with claim 1 in which said light receiving element is a plate which makes it possible to visually observe the position of light reflected at the patient's eye.

5. Slit pattern projecting apparatus comprising objective lens means having an optical axis and means to position a patient's eye in fixed relation to said objective lens means, means for projecting a slit pattern light through said objective lens means to said patient's eye along a slit plane which contains said optical axis of the objective lens means, alignment detecting means comprising optical fiber means and light receiving means including at least one light receiving element located at least in said slit plane at least at one side of the optical axis, said light receiving element being constituted by one end of said optical fiber means.

6. Slit pattern projecting apparatus in accordance with claim 5 which further includes observation optical means having eyepiece means for observing a patient's eye, said optical fiber means being located at the other end in said eyepiece means.

7. Slit pattern projecting apparatus in accordance with claim 5 in which said optical fiber means includes a plurality of optical fibers arranged in a form of a sheet, one end of said sheet being arranged perpendicularly to the slit plane to constitute the light receiving means and the other end constituting observing means.

8. Slit pattern projecting apparatus in accordance with claim 7 in which said sheet of the optical fibers is folded at the other end along center thereof.

* * * * *